United States Patent [19]

Clyde

[11] Patent Number: 4,600,694
[45] Date of Patent: Jul. 15, 1986

[54] APPARATUS FOR HARVESTING CELLS

[76] Inventor: Robert A. Clyde, Station A - Box 6397, New Orleans, La. 70174

[21] Appl. No.: 737,652

[22] Filed: May 24, 1985

[51] Int. Cl.⁴ ............................................. C12M 1/10
[52] U.S. Cl. .................................. 435/312; 435/300; 435/288; 210/151
[58] Field of Search ............... 435/299, 300, 301, 312, 435/288; 210/150, 151, 619

[56] References Cited

U.S. PATENT DOCUMENTS

| | | | |
|---|---|---|---|
| 3,594,277 | 7/1971 | Mako | 435/315 X |
| 4,004,981 | 1/1977 | Hurni et al. | 435/312 X |
| 4,286,065 | 8/1981 | Kaluniants et al. | 435/309 X |
| 4,407,954 | 10/1983 | Clyde | 435/288 X |
| 4,446,236 | 5/1984 | Clyde | 210/150 X |

Primary Examiner—Margaret A. Focarino

[57] ABSTRACT

Apparatus for harvesting converting microorganism cells immobilized on the support discs of a rotary biological contactor. A plurality of cell scraper units are located between the discs and are rotated with the discs while the microorganism cells are growing and performing their converting function. The rotation of the scraper units is then stopped while the discs continue to rotate slowly and the stationary scraper units under controlled pressure scrape the cells off the rotating discs.

7 Claims, 4 Drawing Figures

APPARATUS FOR HARVESTING CELLS

FIELD OF THE INVENTION

The present invention relates to apparatus for treating fluids with converting microorganisms to produce or absorb selected chemicals. More particularly, the invention relates to improved apparatus for harvesting converting bacteria, fungi or algae cells immobilized on a support.

DESCRIPTION RELATIVE TO THE PRIOR ART

It is known that waste water may be treated with selected bacteria, for example, bacteria of the genera Pseudomonas, to remove selected metals such as selenium and uranium. It is also known that selected bacteria in the genera of Zymomonas and Clostridium, as well as fungi in the genera of Kluyveromyces and Saccharomyces, can be used in rotary biological contactors to convert sugar solutions into selected alcohols or acids. It is also known that selected fungi, for example, *Rhizopus arrhizus,* and selected algae, for example, *Chlorella vulgaris* can remove selected metals from aqueous solutions. The fungus Phanerochaeti chrysosporium decolorizes pulp mill effluent but is rather gelatinous and has to be removed from the effluent. Critical factors in such fluid treatment processes are the separation of the bacteria, fungi or algae cells from the treated fluid and the maintenance of the sterility of the process.

Free flowing microorganisms can be separated from the treated fluid by means of a filter. However, because bacteria, fungi and algae cells are very small in size, the pores of the filters must be correspondingly small and quickly become saturated or plugged, requiring exchange or regeneration. Besides being time consuming and expensive, it also means that the fluid must be treated on a non-continuous or "batch" basis.

Immobilizing bacteria, fungi or algae cells on a support, such as fiber discs in a rotary biological contactor (RBC) has many advantages over free flowing cells, including the capability of continuous fluid processing. This can be accomplished, as disclosed in my co-pending U.S. patent application Ser. No. 538,135 entitled "Method For Treating Fluid With Bacteria" filed Oct. 3, 1983. Removal of the immobilized cells from the support discs for further processing can be accomplished in accordance with the aforementioned application by spraying the fiber discs to detach or dislodge the cells from the discs. The detached cells are then washed down to the bottom of the RBC where they can be removed by means of a screw conveyor for recovery of desired materials. Although spraying the cells to dislodge them from the support discs is satisfactory for many applications; it is unsatisfactory in certain applications where spraying is self-defeating as, for example, in a process to recover selected metals or algae from aqueous solutions. Spraying to dislodge the cells from the support discs is also unsatisfactory where the converting microorganism must be maintained in a sterile condition, as for example, in the treatment of sewage sludge in rotary biological contactors. In this process sterile microorganisms carried on rotatable plastic discs degrade and decompose the organic matter in the sludge to innocuous salts and minerals. Solid materials build up rapidly on the discs which are often 10 feet in diameter and set about ½ inch apart. Of approximately 300 installations, there have been more than a dozen shaft failures, so it is very desirable to quickly remove the solids from the discs without effecting sterility.

SUMMARY OF THE INVENTION

In accordance with the present invention, a simple, inexpensive yet thoroughly efficient apparatus is provided for harvesting converting microorganisms and other materials immobilized on a plurality of spaced supports of a rotary biological contactor. This is achieved in accordance with the preferred embodiment of the invention by a plurality of scrapers located in between the supports which rotate with the supports while the microorganisms are growing and performing their converting function. When such converting function is completed or reaches an optimum point, the rotation of the scrapers is stopped while the supports continue their rotation. The pressure which the scrapers exert against the supports is controlled so that the materials adhered to the supports are quickly dislodged without damaging the supports.

The invention and its features and advantages will become more apparent by referring to the accompanying drawings and the ensuing detailed description of the preferred embodiment.

DETAILED DESCRIPTION OF THE INVENTION

Figure 1:
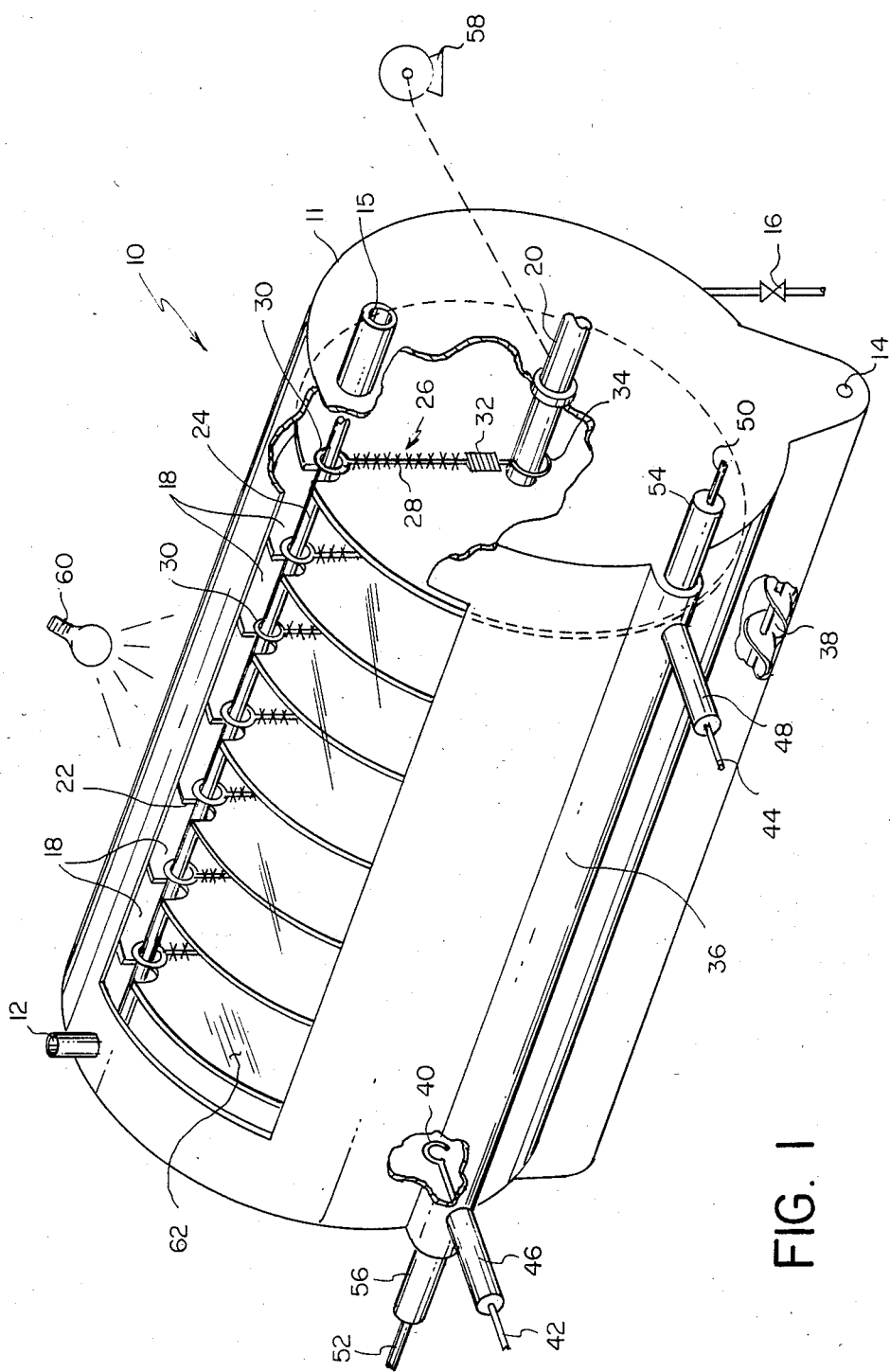
FIG. 1 is a perspective view of a rotary biological contactor constructed in accordance with the present invention.

Because rotary biological contactors are well known, the present description will be directed in particular to elements forming part of or cooperating directly with apparatus in accordance with the present invention. It is to be understood that elements not specifically shown or described may take various forms well known to those having skill in the rotary biological contactor art.

Referring now to the drawings, a rotary biological contactor (RBC) 10 includes a cylindrical tank 11, a nutrient input port 12, a biomass output port 14, a gas output port 15, and an outlet valve 16. A plurality of spaced, supportive discs 18, are made of either plastic or porous fiber webbing materials. Useful disc materials which are preferably resilient include polystyrene and polyethylene, cotton, polyester, orlon, Nylon, rayon acetate, wool, polypropylene or any combination of such materials. The discs 18 are rotatably mounted on a shaft 20. Each of the discs 18 has a U-shaped notch 22 in its outer periphery into which a horizontal rod 24 is received. A microorganism detaching mechanism 26 is located between each pair of spaced discs 18. Each of the detaching mechanisms 26 include a brush 28 whose bristles contact each of the opposed disc surfaces. The bristles are made of stiff Nylon or other suitable material when the supportive discs are made of plastic or soft Nylon or other suitable material when the supportive discs are made of fiber webbing. One end of the brush 28 is attached to a ring collar 30 which is attached to the rod 24. The opposite end of the brush 28 is attached to a spring 32. The spring 32 is in turn attached to a wire 34 which is looped loosely around the shaft 20. The lower portion of the tank 11 includes a U-shaped recess housing 36 adapted to selectively receive the horizontal rod 24 in the manner explained hereinbelow and a screw conveyor unit 38 adapted to remove through port 14 the biomass that is dislodged from the discs 18 by the detaching mechanism 26. A pair of spaced hooks 40 (only one of which is shown in the drawings) adapted to capture the horizontal rod 24 in the manner explained hereinbelow are normally positioned within the U-shaped recess. The hooks 40 are attached to a first set of push rods 42 and 44 which move through double seal units 46 and 48, respectively, attached to the housing 36. The space between the double seals is maintained in a sterilized condition by methods well known to those skilled in the art. A second set of push rods 50 and 52, located at opposite ends of the housing 36, move through similarly sterilized double seal units 54 and 56, respectively, into engagement with the ends of the rod 24.

In operation, the tank 11, support discs 18 and the spaces between the double seals of seal mechanisms 46, 48, 54 and 56 are sterilized by methods well known to those skilled in the art. A suitable bacteria, fungi or algae culture is prepared by sterilizing a nutrient medium, innoculating it with a suitable bacterium, fungus or alga and incubating at a suitable temperature until sufficient cell growth has occurred. The nutrient medium and a selected bacterium, fungus or alga, which will grow on the discs 18 is then pumped into the tank 11 through input port 12.

Useful fungi include species in the genera of Rhizopus which absorb uranium, radium and thorium from aqueous solutions. Useful algae include the alga Spirogyra, Oscillatoria, *Rhizoclonium Hydrodictyon*, Cladophora and *Chlorella vulgaris* which can remove several metals, including molybdenum, selenium, uranium, radium and gold from aqueous solutions. Useful bacteria include species of the genera Pseudomonas, species of the genera Bacillus, and species of the genera Hyphomicrobium, which can remove metals including manganese, gold, silver, selenium, uranium and radium from aqueous solutions. Other useful bacteria include species in the genera of Zymomonas species is the genera of Clostridium and species in the genera of Kluyveromyces, which can convert sugar solutions into selected alcohols or acids. Yogurt can be removed with cells of Lactobacillus.

Figure 2:
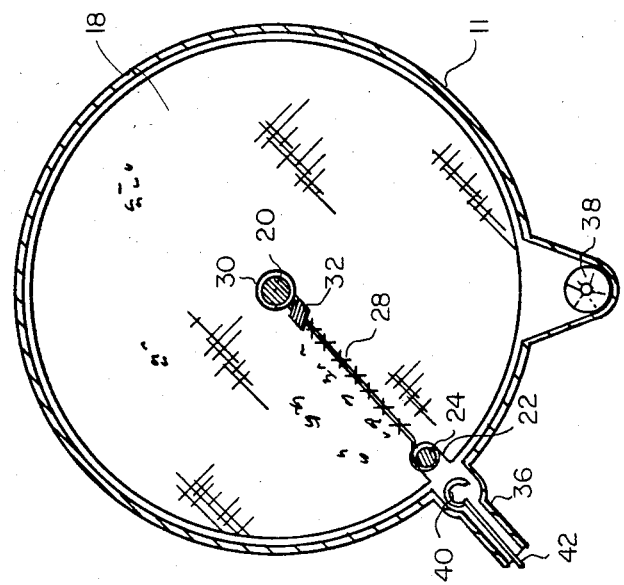

The shaft 20 and discs 18 are rotated by motor 58 for a period of time sufficient to produce cell growth and attachment to the discs. As shown in FIG. 2, the horizontal rod 24 is positioned during this rotation in the disc notches 22 and, as a result, the detaching mechanisms 26 rotate in synchronism with the discs.

Figure 3:
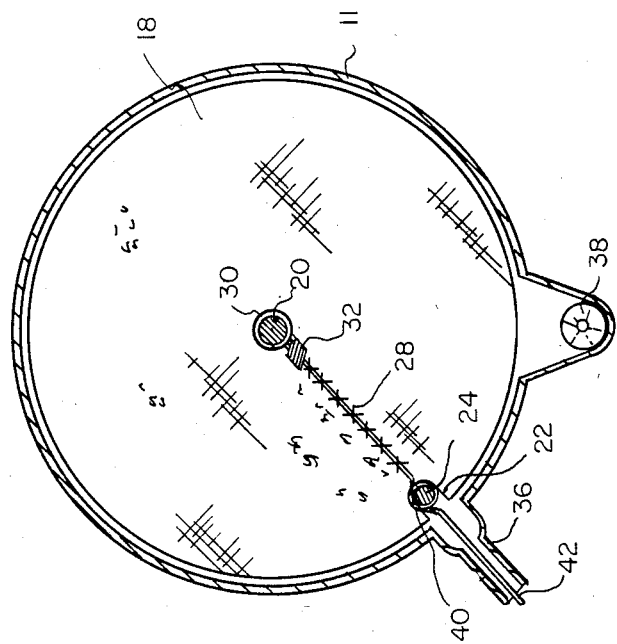
FIGS. 2-4 are cross sectional views of the rotary biological contactor illustrated in FIG. 1 showing the various operational positions of the cell detaching mechanism.
Figure 4:
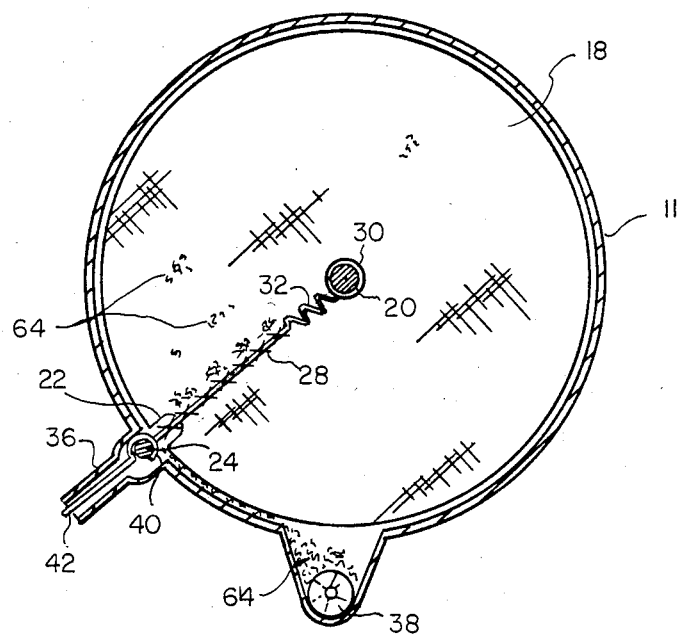

If, for example, the RBC 10 is being used to remove a metal from waste fluid, the nutrient medium then is drained through the valve 16. The waste fluid is pumped into the RBC through input port 12 and stirred by the rotation of the discs 18 and detaching mechanisms 26 until the metal attaches to the microorganisms. When the attachment process is complete or has reached an optimum point, the waste fluid is drained from the RBC 10 through the valve 16. The rotation of the RBC is then slowed and the push rods 42 and 44 are pushed forwardly (by means not shown) causing the hooks to leave housing 36 and move into the tank 11. When the hooks 40 engage the rod 24, as shown in FIG. 3, rotation is stopped and the push rods 42 and 44 are pulled backwardly, pulling the rod 24 into the housing as shown in FIG. 4. Rotation is then started again slowly at 2 or 3 rpm and the now stationary brushes 28 scrape the materials 64 adhering to the discs 18 down to the screw conveyor unit 38. If it is desired to scrape harder against the disc surfaces being scraped by the brushes 28, the appropriate one of the two push rods, 50 or 52, is pushed inwardly against the horizontal rod 24. When the rod 50 or the rod 52 is pushed inwardly, the brushes 28 are forced against and stretch one of the resilient support discs 18. After a very short harvest time, usually less than one minute, the push rod 50 or 52 is withdrawn causing the resilient support disc to snap back to its original shape. This snapping action is effective in dislodging materials adhered to the disc 18 which were not removed by the scraping action. When push rod 50 or 52 is withdrawn, the push rods 40 and 42 are pushed forwardly so that the hooks 40 move back into the tank 11 releasing the rod 24 for return to its position within the disc notches 22. The operation can now be continued because the sterility of the RBC has been maintained.

If the RBC 10 is used to grow algae, a lamp 60 is shined into a transparent top portion 62 of the tank 11. To produce pulsating light, a plurality of wires (not shown) can be placed across the top of the transparent section 62. If the RBC 10 is used to grow fungi, sterile air is bubbled into the tank 11 through valve 16.

The invention has been described in detail with particular reference to a preferred embodiment thereof, but it will be understood that variations and modifications can be effected within the spirit and scope of the invention.

I claim:

1. In a rotary biological contactor of the type adapted to treat fluids with converting microorganisms and having a rotatable shaft upon which are mounted a plurality of spaced supports on which the converting microorganisms can be immobilized and brought into contact with the fluid to be treated, a mechanism for physically detaching the converting microorganism from the supports and a mechanism for removing detached microorganisms from the contactor, the improvement wherein said detaching mechanism comprises a plurality of spaced scrapers located in between the supports, means for rotating the scrapers in synchronism with the supports, means for selectively stopping the rotation of the scrapers while permitting the continued rotation of the supports, and control means for controlling the pressure which the scrapers exert against the supports.

2. The apparatus according to claim 1, wherein said scrapers comprise fiber brushes.

3. The apparatus according to claim 2, wherein said fibers of said brushes consist of Nylon.

4. The apparatus according to claim 1, wherein said scraper rotating means comprises a support rod, a plurality of collar members attached to the support rod, each of the collar members being located between a pair of spaced microorganism supports and attached to one end of a scraper, a corresponding plurality of springs biased to pull the support rod into contact with the microorganism supports each of the springs being attached to the opposite end of a scraper, and a corresponding plurality of wire members, each of the wire members having one end wrapped loosely around said rotatable shaft and the opposite end attached to a spring.

5. The apparatus according to claim 4, wherein said means for selectively stopping the rotation of the scrapers comprises means for pulling said support rod away from the microorganism supports against the bias of said springs and means for holding said support rod stationary.

6. The apparatus according to claim 5, wherein said control means comprises first push rod means adapted to selectively engage and withdraw said support rod away from the supports so as to stretch said springs and second push rod means adapted to selectively push against said support rod.

7. The apparatus according to claim 1, wherein said microorganism supports are resilient and said detaching mechanism further comprises means for stretching the resilient microorganism supports and then allowing the supports to snap back to their original shapes.

* * * * *